United States Patent
Morgan et al.

(10) Patent No.: US 6,227,857 B1
(45) Date of Patent: May 8, 2001

(54) DENTAL AND ORTHOPEDIC IMPLANT SYSTEM

(75) Inventors: Vincent J Morgan, Boston, MA (US); Thomas D Driskell, Westerville, OH (US)

(73) Assignee: Vincent Morgan, Boston, MA (US)

(*) Notice: Subject to any disclaimer, the term of this patent is extended or adjusted under 35 U.S.C. 154(b) by 0 days.

(21) Appl. No.: 09/341,283

(22) PCT Filed: Jan. 26, 1998

(86) PCT No.: PCT/US98/01353

§ 371 Date: Jul. 9, 1999

§ 102(e) Date: Jul. 9, 1999

(87) PCT Pub. No.: WO98/34562

PCT Pub. Date: Aug. 13, 1998

Related U.S. Application Data

(60) Provisional application No. 60/037,540, filed on Feb. 11, 1997.

(51) Int. Cl.[7] ............................................. A61C 8/00
(52) U.S. Cl. ................................................ 433/173
(58) Field of Search ................................. 433/172, 173, 433/174, 175, 176

(56) References Cited

U.S. PATENT DOCUMENTS

| | | | | |
|---|---|---|---|---|
| 4,466,796 | * | 8/1984 | Sandhaus | 433/173 |
| 4,738,623 | * | 4/1988 | Driskell | 433/173 |
| 5,078,607 | * | 1/1992 | Niznick | 433/173 X |
| 5,254,005 | * | 10/1993 | Zuest | 433/173 |
| 5,310,343 | * | 5/1994 | Hasegawa et al. | 433/173 |

* cited by examiner

*Primary Examiner*—Nicholas D. Lucchesi

(57) ABSTRACT

A dental or orthopedic implant (10, 10', 100, 100', 200) having an abutment receiving bore either with a self-holding taper or threaded is shown which in selected embodiments includes annular epithelial stops (32, 132, 232) to limit epithelical migration. Other embodiments useful as posterior implants or where minimal bone depth is available (100, 100', 200, 300, 400) have a wide body with a shortened length having a length (l) to width (w) ratio of no more than approximately 1.5:1 and configured so that the outer body distributes lateral forces all along the side wall and distal end face (18) abetted in selected embodiments by a load bearing groove (126, 226) in the distal end face of the implant. Osseointegration promoting structures are shown including fins (24), evenly distributed dimples (250) and coatings (302) in selected embodiments.

20 Claims, 5 Drawing Sheets

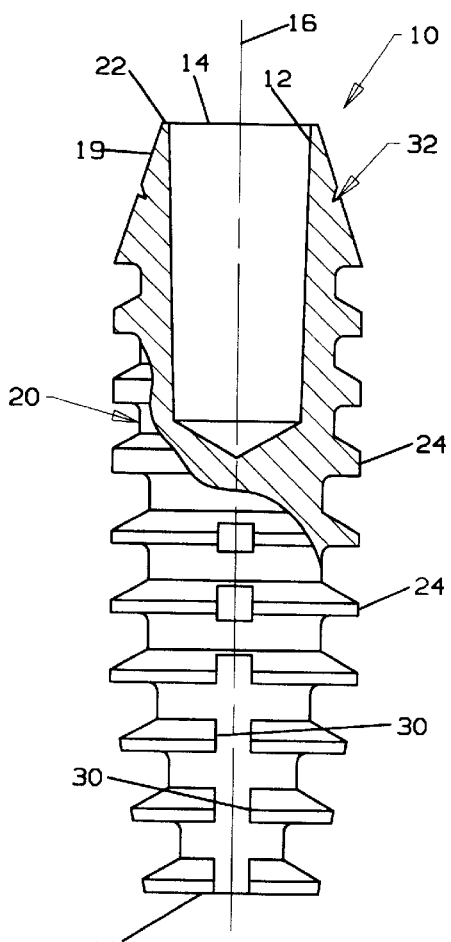
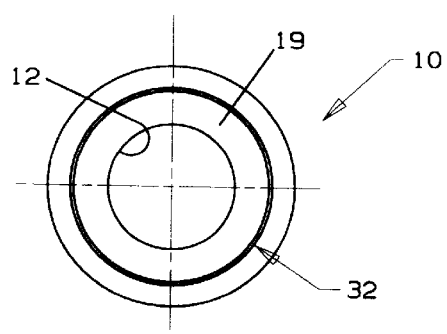
FIG 1
FIG 2
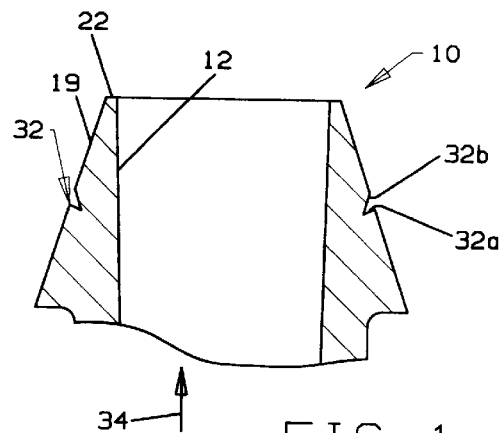
FIG 1a
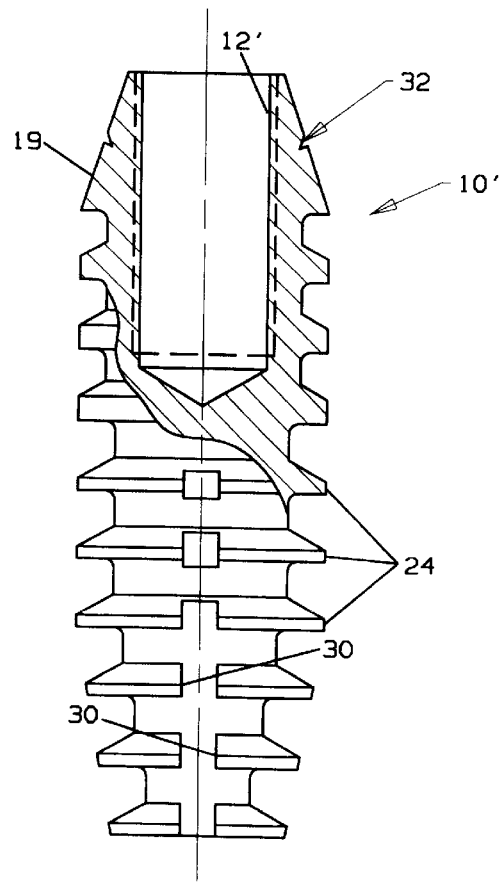
FIG 3

DENTAL AND ORTHOPEDIC IMPLANT SYSTEM

CROSS REFERENCE TO RELATED APPLICATIONS

This application is a 371 of PCT/US98/01353, filed Jan. 26, 1998 claiming the benefit of provisional application No. 60/037,540, filed Feb. 11, 1997.

FIELD OF THE INVENTION

This invention relates generally to restorative dentistry and more particularly to improved dental implant systems.

BACKGROUND OF THE INVENTION

Natural teeth may be lost as a result of dental disease or trauma making it desirable for replacement with prosthetic devices. One type of prosthetic device is a dental implant or root member which is surgically positioned within the mandibular or maxillary alveolar bone. After healing a head member or abutment is mounted on the implant and then, in turn, a tooth-simulating prosthesis, or crown, is mounted on the abutment.

In preparing a site for a generally cylindrical implant a bore having a diameter generally the same as the diameter of the implant is drilled in the aveolar bone. The implant is positioned in the bore and, for an implant type positioned below the surface of the bone, is packed with autogenous graft material, such as bone particles harvested during the drilling procedure. The implant is provided with an abutment receiving bore which is closed with a temporary healing plug and the site is covered and allowed to heal for a suitable period of time, e.g., 3–6 months to allow for osseointegration with the bone and the implant forming essentially a unitary body. After the healing and bone growth process the temporary healing plug is surgically accessed and removed. A permanent abutment having a post portion receivable in the bore of the implant is then mounted on the implant.

In the early stages of the development of dental implants a typical failure mode comprised the migration of epithelium along the sides of the implant causing bone loss until eventually the implant would fall out or break due to increased leverage forces. The advent of various grooves and laterally extending fins which promote osseointegration has largely overcome this problem, however, typically there is still some epithelial migration and concomitant bone loss at the crestal end of the implant. This tendency is exacerbated if there is any motion between the implant and the abutment.

In one type of implant system the abutment is threadingly attached to the implant. Although the screw threads are manufactured with very tight tolerances to minimize any looseness there is inherently a certain amount of micro-motion between the screw portion and the threaded bore of the implant to enable the screw to be screwed into the implant. This micro-motion and bacterial leakage between the components cause bone cratering and soft tissue attachment migration leading to further deterioration.

Another dental implant system utilizes an abutment having a post formed with a locking or self-holding taper which is received in the bore of the implant which is formed with a matching locking taper. In this type of system once the post is engaged in the bore of the abutment there is no motion whatsoever between the two members. A system of this type is shown and described in co-assigned U.S. Pat. No. 4,738,623, the subject matter of which is incorporated herein by this reference. In this patent an implant is shown having multiple, outwardly extending fins formed on the lower portion thereof and has a narrowed upwardly and inwardly contoured shoulder formed above the fins. In this system epithelial migration and bone loss is found to be limited to the top portion of the shoulder unless the patient has some systemic problem, e.g., the patient is a diabetic or a smoker.

It is an object of the present invention to provide a dental implant system having means to limit epithelial migration which can be used with implant systems employing either threaded engagement members or locking taper engagement members.

Another object of the invention relates to implants intended for posterior placement or other areas where minimal bone depth is available. Normally, the relatively long length of an implant provides a favorable length to width ratio which enables the implant to withstand the high lateral loading to which the implant is subjected. However, at the posterior part of the oral cavity, as well as other parts of the body, the depth of the bone is frequently insufficient for a normal length implant. Further, in the posterior section the lateral forces are greatest while at the same time the length to width ratio is decreased thereby resulting in a greater propensity toward implant failure.

SUMMARY OF THE INVENTION

It is, therfore, an object of the present invention to provide a dental implant system which overcomes the above noted limitations of the prior art.

Briefly, in accordance with the invention, a dental implant comprises a body formed of biocompatible material having an abutment receiving bore extending from a crestal end along a longitudinal axis toward a distal end. The implant includes at least one epithelial stop comprising an annular surface circumscribing the body. One selected location for an epithelial stop is shown located intermediate the ends of a frustoconical shoulder formed between the outer side wall of the implant and the crestal end face of the implant. Another selected location for an epithelial stop is shown located between the shoulder and an outwardly extending fin. The epithelial stops are particularly advantageous for use with abutments having threaded means coupling the implant and abutment which tend to be subject to micro-motion but can also be used with locking taper coupling means.

According to another embodiment of the invention an implant is provided which is particularly suitable for use as a posterior implant subject to relatively high lateral force loading by having an increased width with a length to width ratio of no greater than approximately 1.5 to 1. The posterior implant utilizes its unique squat configuration to distribute lateral forces generally throughout its outer envelope.

Additional objects and features of the invention will be set forth in part in the description which follows and in part will be obvious from the description. The objects and advantages of the invention may be realized and attained by means of the instrumentalities and combination particularly pointed out in the appended claims.

BRIEF DESCRIPTION OF THE DRAWINGS

The accompanying drawings, which are incorporated in and constitute part of the specification, illustrate preferred embodiments of the invention and, together with the description, serve to explain the objects, advantages and principles of the invention. Dimensions of certain of the parts may have been altered for the purpose of illustration. In the drawings:

FIG. 1 is an enlarged front elevational view, partly in cross section, of a dental implant made in accordance with a first embodiment of the invention;

FIG. 1a is a further enlarged portion of FIG. 1;

FIG. 2 is a top plan view of the FIG. 1 implant;

FIG. 3 is a view, similar to FIG. 1, of a modified first embodiment of the invention;

DETAILED DESCRIPTION OF PREFERRED EMBODIMENTS

Figure 4:
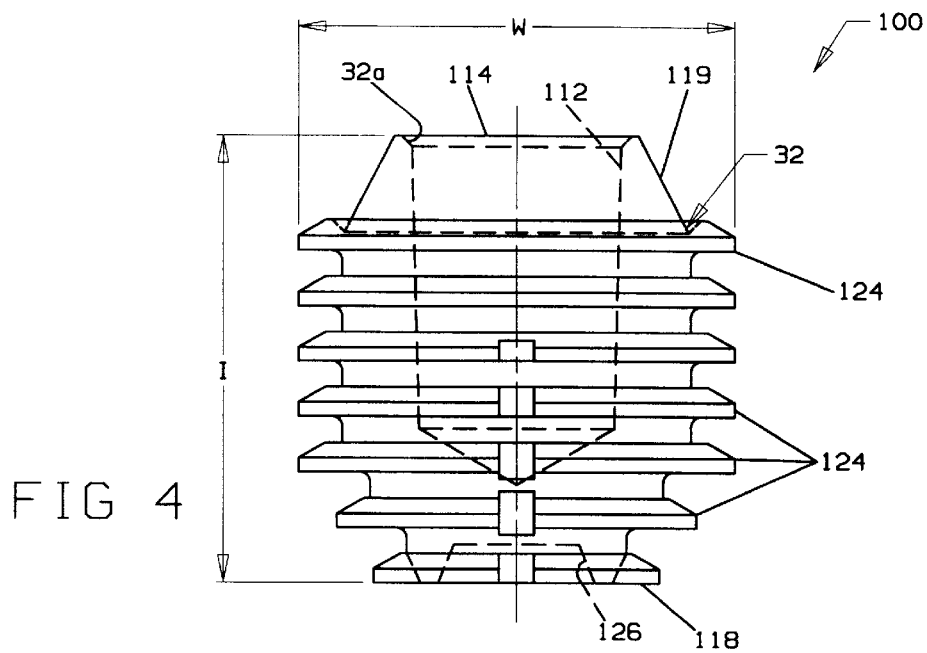
FIG. 4 is an enlarged front elevational view of an implant made in accordance with a second embodiment of the invention and also incorporating a feature of the first embodiment.

With regard to FIGS. 1, 1a and 2 a dental implant made in accordance with the invention is referenced by numeral 10. Implant 10 is composed of biocompatible material such as titanium or a titanium alloy having a generally cylindrical body and is formed with a closed ended bore 12 having a locking taper extending from a crestal end face 14 along a longitudinal axis 16 toward an opposite distal end face 18. A smooth surfaced shoulder 19, such as frustoconical as shown, extends from crestal end face 14, adjacent bore 12, to the main body portion 20. A narrow rim 22 may be provided at the crestal end between bore 12 and shoulder 19.

Main body portion 20 is shown provided with a surface configuration which promotes osseointegration comprising a plurality of laterally extending fins 24. If desired, some or all the fins may be provided with one of more slots 30 to inhibit relative rotation of implant 10 in the aveolar bone. Main body portion 20, including fins 24, preferably has a slightly decreasing diameter towards distal end face 18.

Epithelial migration tends to follow surfaces inwardly toward the center of an opening and away from a crestal end of the opening and, as mentioned above, in the case of an implant, can cause loss of bone supporting the implant. As shown in FIGS. 1 and 1a an epithelial stop is provided to limit such migration. As shown in FIGS. 1 and 1a, groove 32 circumscribes shoulder 19 intermediate its upper and lower extremities and comprises an annular surface portion 32a which forms a sharp angle with shoulder 19, e.g., a right or acute angle and annular surface 32b which forms an acute angle with surface 32a. Annular surface 32b forms a first surface portion which extends from the outer surface of the implant to the inner part of the groove in a direction toward a plane perpendicular to the longitudinal axis which intersects the distal end of the implant and annular surface 32a forms a second surface portion which extends from the inner part of the groove toward a plane perpendicular to the longitudinal axis which intersects the crestal end and which meets the outer surface of the implant on the distal end side of the groove. This surface 32a extends in a direction which is both outwardly away from the center (longitudinal axis 16) and upwardly away from distal end 18 when compared to the direction in which epithelium would migrate from crestal end 14 down shoulder 19. To be effective as an epithelial stop surface 32a should extend at least 0.001 inch and preferably at least 0.005 inch. As mentioned supra, in most cases in a locking taper system, even without the epithelial stop, migration is limited to the upper portion of shoulder 19. However, epithelial stop 32 serves to prevent further migration in extreme cases, such as those mentioned above relating to systemic problems.

Figures 4A, 4B:
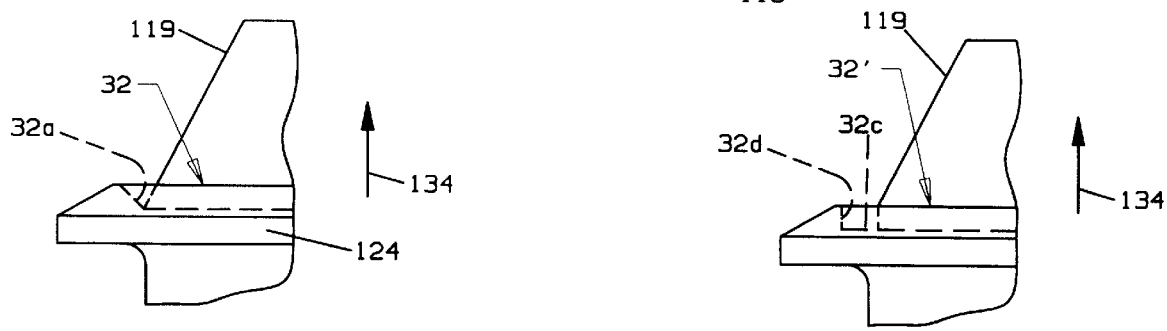
FIGS. 4a and 4b are broken away, enlarged views of a portion of FIG. 4 showing two different epithelial stops made in accordance with the invention.
Figure 5:
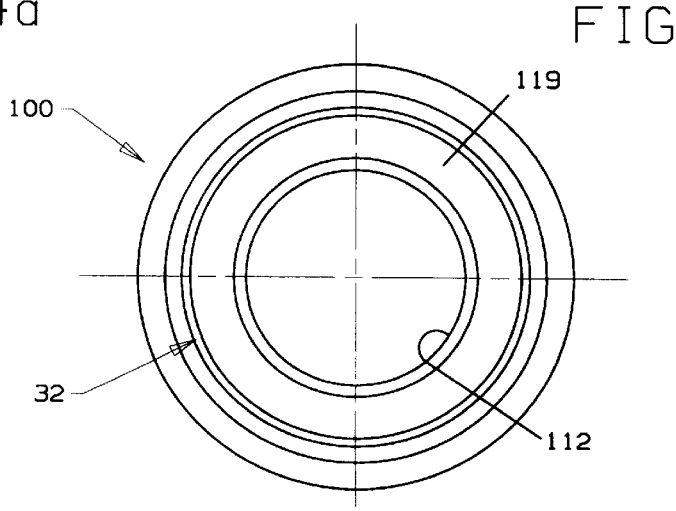
FIG. 5 is a top plan view of the FIG. 4 implant.
Figure 6:
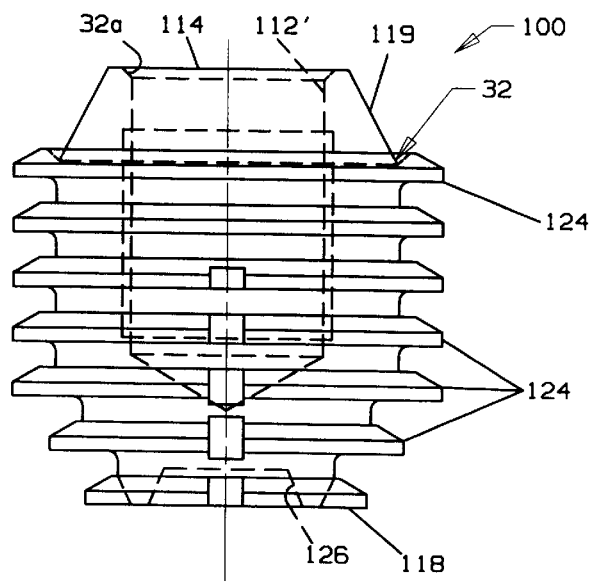
FIG. 6 is a view, similar to FIG. 4, of a modified implant made in accordance with the second embodiment of the invention also including a feature of the first embodiment.

Other locations for the stop surface can be selected, for example, as shown in FIGS. 4–6. In FIG. 4 an implant 100 is shown which has first and second epithelial stops 32, the first stop comprises a frustoconical surface 32a extending from bore 112 outwardly and upwardly toward crestal end 114. Thus epithelium migrating from an abutment mounted on implant 10 would have to work its way from the post received in bore 112 upwardly, as shown in FIG. 4, and outwardly. A second stop or groove 32 is located between shoulder 119 and the closest fin 124 to the crestal end face 114. Groove 32 of the second stop has a frustoconical surface 32a extending toward the crestal end face in the direction of arrow 134 and outwardly away from the center as shown in FIG. 4a in the same manner as surface 32a of FIG. 1a and surface 32a in FIG. 4 extending from bore 112 or it can take the form of a compound surface such as a square groove as shown in FIG. 4b. With reference to FIG. 4b the epithelial stop 32' is a square groove with a first surface 32c extending radially outwardly and a second cylindrical surface 32d extending in a direction from distal end face 118 toward crestal end face 114, i.e., in the direction of arrow 134. For most effective performance both first surface 32c and second surface 32d should extend at least approximately 0.001 inch, and preferably 0.005 inch, radially outwardly and longitudinally respectively.

Going back to FIG. 3, implant 10' comprises the same structure as FIG. 1 except for the abutment receiving bore 12' which in FIG. 3 is shown to be threaded for reception of a threaded portion of an abutment. In this embodiment the epithelial stop is particularly useful in view of the greater potential for migration due to the micro-motion between the abutment and implant members inherent in a threaded system as mentioned above.

Figure 7:
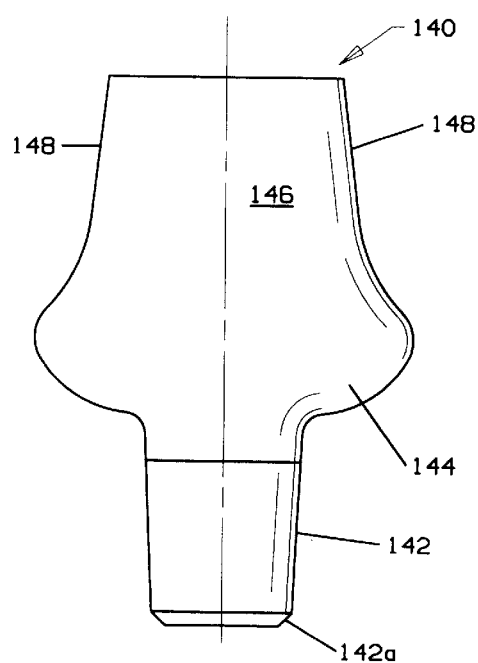
FIG. 7 is a front elevational view, enlarged to a slightly less degree than FIG. 4, of an abutment useful with the FIG. 4 implant.
Figure 8:
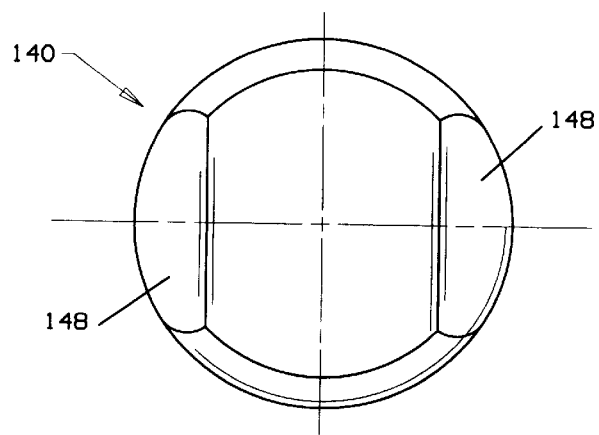
FIG. 8 is a top plan view of the FIG. 7 abutment.

With reference to FIGS. 7 and 8, abutment 140 comprises a post portion 142 having a locking taper matching that of bore 12 of implant 10 extending down from a base 144, the lower portion of which is shaped generally as a portion of a sphere. The upper portion 146 of base 144 serves to receive a prosthesis and is preferably provided with an anti-rotational configuration such as opposed flats 148. Preferably post 142 is provided with a slight chamfer 142a to facilitate placement of post 142 in bore 12.

Figure 9:
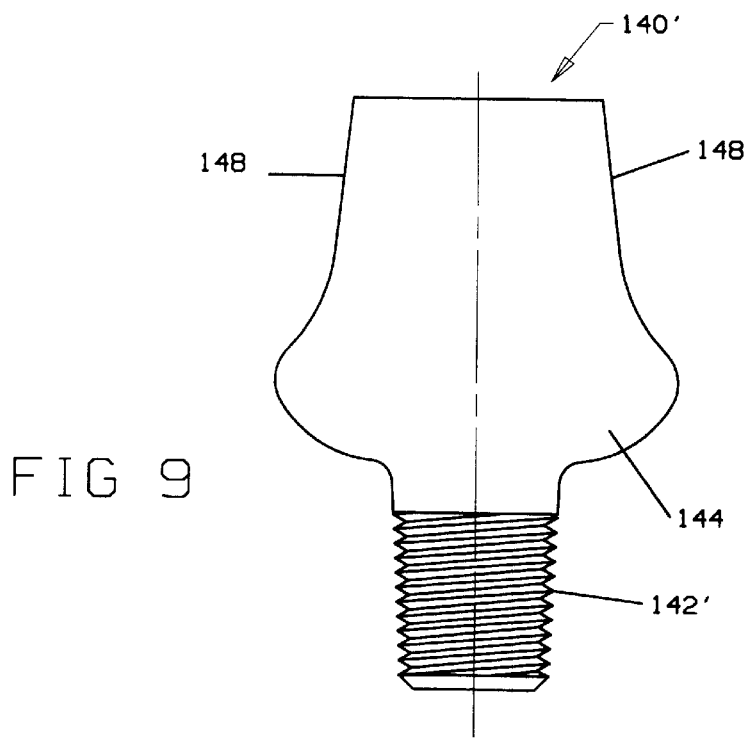
FIG. 9 is a view, similar to FIG. 7 but drawn to a slightly less degree of enlargement than FIG. 7, of a modified abutment useful with the FIG. 6 implant.

FIG. 9 shows a corresponding abutment 140' having a threaded post 142' adapted for use with threaded bore 12' of implant 10' (FIG. 3) but is otherwise identical therewith.

Referring to FIGS. 4–6 an aspect of the invention will now be described relating to structure particularly adapted for use in the posterior regions of the aveolar bone or other areas where minimal bone depths occur, for example, the spine. As noted previously, the typical implant has a relatively high length to diameter, or width, ratio thereby providing effective resistance to lateral loading. Such ratios typically are on the order of 2:1 or higher. By way of example, a currently available family of implants includes a small diameter of 3.5 mm, an intermediate diameter of 4 mm and a large diameter of 5 mm and having lengths of 8 mm, 11 mm or 14 mm, as desired. The corresponding length to width ratios range from a low of 1.6:1 to a high of 4.0:1. However, in the posterior portion of the aveolar bone there often is not sufficient bone depth to permit the use of such long implants. This problem is exacerbated in that the forces generated at this portion of the aveolar bone are significantly greater than at the anterior portion. In accordance with the invention implant 100 having a locking taper abutment receiving bore 112 and implant 100' having a threaded abutment receiving bore 112' are made wider than conventional implants with the diameter of post 142,142' of the corresponding abutment also being increased, for example, from 2 mm to 3 mm. A typical width, or diameter, w shown in FIG. 4, is approximately 6 mm and the length or height l being any one of several lengths useful for different individuals. For example, a family of posterior implants made in accordance with the invention includes a short length of 6 mm, a medium length of 6.75 mm and a long length of 8.25 mm resulting in ratios of 1:1, 1.25:1 and 1.375:1, respectively. Thus the length to width ratio of implants made in accordance with this embodiment is no greater than approximately 1.5:1.

The squat configuration of the implant, whose lower outer surface approximates a spherical configuration, provides improved resistance to lateral loading. In addition to fins 124 there is a load bearing groove 126 formed in the bottom or distal end face 118 of implants 100, 100'. Any lateral load applied to the implant through an abutment mounted in bore 112,112', due to the squat configuration, will be distributed in compression and tension components all along the outer surface by means of fins 124 abetted by groove 126 in the distal end face 118.

Figure 10:
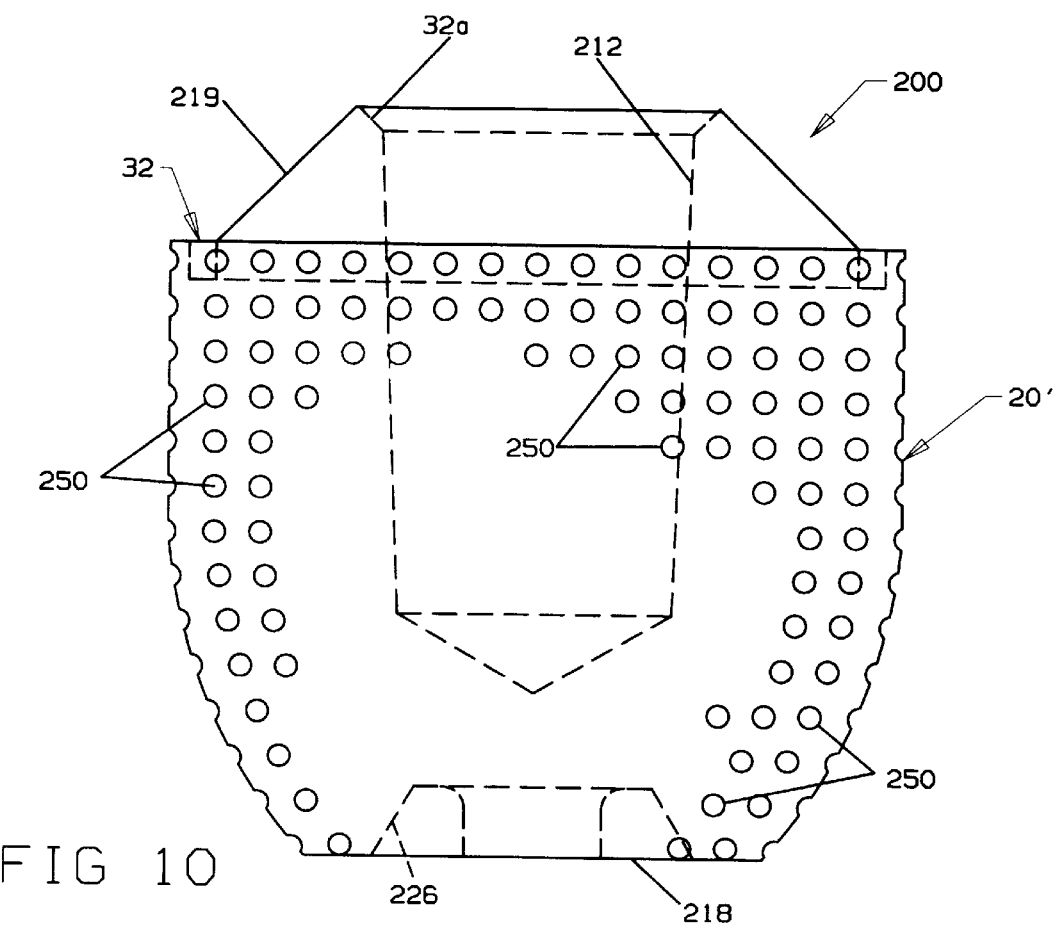
FIGS. 10 and 11 are front elevational views of modified implants made in accordance with the second embodiment of the invention also including a feature of the first embodiment.
Figure 11:
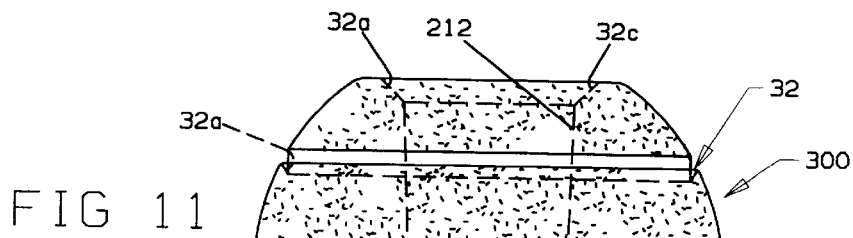
Figure 12:
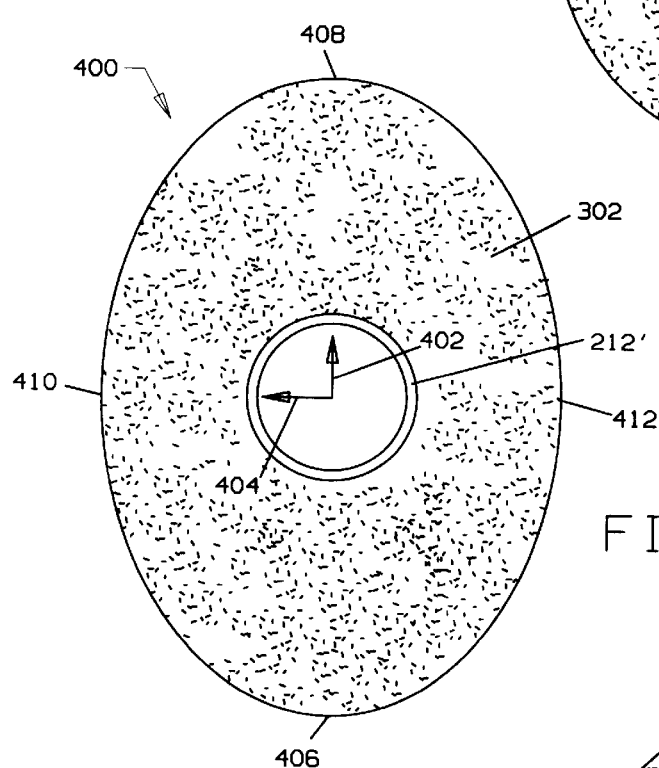
FIGS. 12 and 13 are, respectively, a top plan view and an elevational view taken in the direction of arrow 402 in FIG. 12 of yet another modified implant made in accordance with the second embodiment of the invention.
Figure 13:
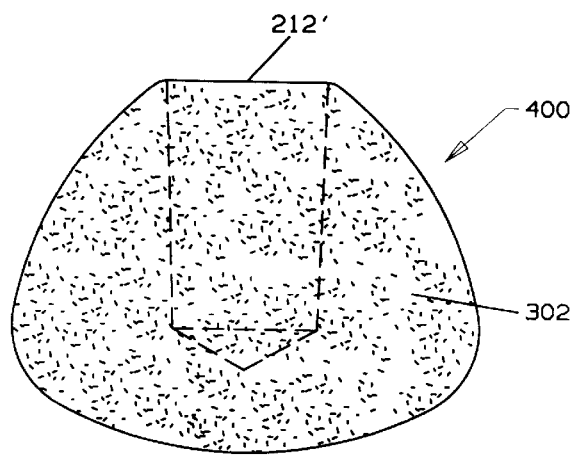

Although fins are shown in FIGS. 1, 3, 4, and 6 as the primary mechanism to promote osseointegration the outer surface could also be formed with a plurality of preferably evenly spaced dimples 250 shown in implant 200 in FIG. 10 having depth of at least approximately 0.005 inch with or without a suitable coating of hydroxyapatite or the like to further promote osseointegration. Bore 212 is shown as a locking taper however the dimpled surface could be used with virtually any type of implant system including those employing threaded coupling members. FIGS. 11–13 show additional modified implants of the FIGS. 4–6 embodiment. In FIG. 11 implant 300 is shown which is essentially spherical to optimize distribution in any direction of any lateral loading from an implant. Implant 300 is shown with an outer surface having a coating 302 of suitable osseointegration promoting material such as hydroxyapatite although it will be understood that any suitable osseointegration promoting surface can be employed. Various curved configurations, both symmetrical and asymmetrical can be utilized to derive the benefit of improved distribution of lateral loading such as implant 400 of FIGS. 12 and 13 which has a generally ellipsoidal configuration. The intersection of a plane drawn perpendicular to longitudinal axis 16 and implant 400 forms an ellipse, as seen in FIG. 12, with the major axis extending in the direction of arrow 402 between points 406,408, called width herein, and the minor axis extending in the direction of arrow 404 between points 410,412, called depth herein. It will be understood that, if desired, one or more epithelial stops 32, 32' may be provided to limit epithelial migration in the same manner as described in the previous modified embodiments.

Although the depths of the FIGS. 4–12 implants as viewed in the bucal-lingual (arrow 404) direction—the distance between points 410 and 410—does not need to match the width—the distance between points 406 and 408—, the ratio of depth to width should be sufficient to provide the desired lateral force distribution resulting from the curved surface in accordance with the invention.

Although the invention has been described with regard to specific preferred embodiments thereof, variations and modifications will become apparent to those skilled in the art. It is therefore the intention that the appended claims be interpreted as broadly as possible in view of the prior art to include all such variations and modifications for use as a dental implant as well as for all orthopedic implants such as spinal fixation implants and cranial appedages.

What is claimed:

1. An implant for a living body comprising a body having a longitudinal axis and having a crestal end face and a distal end face spaced along the axis, an abutment receiving bore formed through the crestal end face and extending into the body along the axis to a closed end, the body having an outer surface disposed between the crestal end face and the distal end face, and at least one epithelial stop comprising an annular groove having an inner part circumscribing the body and having an axis of rotation generally coincident with the longitudinal axis, the annular groove having a depth at least approximately 0.001 inch and being formed by a first annular surface portion which extends from the outer surface on the crestal end face side of the groove to the inner part of the groove in a direction toward a plane perpendicular to the longitudinal axis which intersects the distal end face and a second annular surface portion which extends from the inner part of the groove in a direction toward a plane perpendicular to the longitudinal axis which intersects the crestal end face until it meets the outer surface of the body on the distal end face side of the groove.

2. An implant according to claim 1 in which the body is formed with a generally frustoconical shoulder having a smooth surface extending from an upper end at the crestal end face to a lower end and the annular groove of the at least one epithelial stop is located on the shoulder intermediate the upper and lower ends thereof.

3. An implant according to claim 2 in which the second annular surface portion of the annular groove of the at least one epithelial stop is generally flat and forms an angle of one of approximately 90 degrees and less than 90 degrees with the shoulder on the side thereof closest to the distal end face and the first annular surface portion is generally flat and forms an acute angle with the second annular surface portion.

4. An implant according to claim 1 in which the body is formed with a shoulder having a smooth surface extending from an upper end at the crestal end face to a lower end and further comprising retention means formed on the outer surface to facilitate osseointegration in which the retention means includes a plurality of fins extending outwardly from the body between the shoulder and the distal end face.

5. An implant according to claim 4 in which the first annular surface portion of the annular groove of the at least one epithelial stop is formed by a continuation of the shoulder extending into a contiguous fin.

6. An implant according to claim 4 in which the retention means comprises a plurality of generally evenly spaced depressions in the outer surface having a depth of at least approximately 25 micron.

7. An implant according to claim 1 in which the annular groove of the at least one epithelial stop is a square groove approximately 0.005 inch deep.

8. An implant according to claim 1 in which the abutment receiving bore is formed with a screw thread for threading reception of a threaded post of an abutment.

9. An implant according to claim 1 in which the abutment receiving bore is formed with a locking taper for locking reception of an abutment post having a matching locking taper.

10. An implant comprising a body having a longitudinal axis and having a length l between a crestal end face and a distal end face spaced along the axis, the body having a width w taken in a direction perpendicular to the longitudinal axis, an abutment receiving bore formed through the crestal end face and extending into the body along the longitudinal axis to a closed end, the ratio of length l to width w being no greater than approximately 1.5:1.

11. An implant according to claim 10 in which l is approximately 6 mm and w is approximately 6 mm.

12. An implant according to claim 11 in which the abutment receiving bore is approximately 3 mm in diameter and is formed with a locking taper.

13. An implant according to claim 12 further including at least one epithelial stop comprising an annular groove circumscribing the body and having an axis of rotation coincident with the longitudinal axis, the annular groove having a depth of at least approximately 0.001 inch and being formed by a first annular surface portion which extends from the outer surface on the crestal end face of the groove to an inner part of the groove and a second annular surface portion which extends from the inner part of the groove in a direction toward a plane perpendicular to the longitudinal axis which intersects the crestal end face until it meets the outer surface of the body on the distal end face side of the groove.

14. An implant according to claim 13 further comprising a shoulder having a frustoconical configuration extending from the crestal end face and the annular groove of the at least one epithelial stop is located on the shoulder.

15. An implant according to claim 13 further comprising a shoulder having a frustoconical configuration extending from the crestal end face and retention means are formed on the body comprising a plurality of spaced, outwardly extending fins in which the first annular surface portion of the annular groove of the at least one epithelial stop is formed by a continuation of the shoulder extending into a contiguous fin.

16. An implant according to claim 10 further comprising a circular load bearing groove formed in the distal end face.

17. An implant according to claim 10 in which the abutment receiving bore is formed with a screw thread for threading reception of a threaded post of an abutment.

18. An implant according to claim 10 in which the abutment receiving bore is formed with a locking taper for locking reception of an abutment post having a matching locking taper.

19. An implant according to claim 10 further including retention means comprising a plurality of generally evenly spaced depressions in the outer surface each having a depth of at least approximately 25 microns.

20. An implant for a living body comprising a body having a longitudinal axis and having a crestal end face and a distal end face spaced along the axis, an abutment receiving bore formed through the crestal end face and extending into the body along the axis to a closed end, the body having an outer surface disposed between the crestal end face and the distal end face, and at least one epithelial stop comprising an annular groove having an inner part circumscribing the body and having an axis of rotation generally coincident with the longitudinal axis, the annular groove having a depth at least approximately 0.001 inch and having an annular surface portion which extends from the inner part of the grove in a direction toward a plane perpendicular to the longitudinal axis which intersects the crestal end face until it meets the outer surface of the body on the distal end face side of the groove.

* * * * *